United States Patent [19]

Mueller et al.

[11] Patent Number: 5,151,441
[45] Date of Patent: Sep. 29, 1992

[54] 3-ISOXAZOLYLBENZYL ESTERS, THEIR PREPARATION AND THEIR USE

[75] Inventors: Stefan Mueller, Speyer; Hans Theobald, Limburgerhof; Bernd Wolf, Fussgoenheim; Peter Hofmeister, Neustadt; Uwe Kardorff, Mannheim; Christoph Kuenast, Otterstadt, all of Fed. Rep. of Germany

[73] Assignee: BASF Aktiengesellschaft, Ludwigshafen, Fed. Rep. of Germany

[21] Appl. No.: 699,528

[22] Filed: May 14, 1991

[30] Foreign Application Priority Data

May 18, 1990 [DE] Fed. Rep. of Germany ....... 4016049

[51] Int. Cl.$^5$ .................. A01N 43/80; C07D 413/04; C07D 261/06; C07D 277/20
[52] U.S. Cl. ..................... 514/378; 514/380; 546/275; 548/206; 548/235; 548/243; 548/247; 548/248; 548/202
[58] Field of Search ............... 548/247, 243, 248, 235, 548/206, 202; 546/275; 514/378, 380

[56] References Cited

U.S. PATENT DOCUMENTS

| | | | |
|---|---|---|---|
| 4,153,707 | 5/1979 | Moon | 424/272 |
| 4,426,524 | 1/1984 | Plummer | 544/336 |
| 4,689,342 | 8/1987 | Tessier et al. | 524/427 |

FOREIGN PATENT DOCUMENTS

| | | | |
|---|---|---|---|
| 0110769 | 6/1984 | France | 544/336 |
| 1398103 | 6/1975 | United Kingdom | 548/247 |

OTHER PUBLICATIONS

CA113:171868v. Preparation of . . . anticholesteremics. Takezawa et al. May 17, 1990.
CA 110, Formula Index, 1137f, 1990.
PCT Patent-WO 82/01368, Plummer, Oct. 20, 1980.
J. Agric. Food Chem. 1984, 32. 1116–1121, Plummer et al.

Primary Examiner—Mary C. Lee
Assistant Examiner—Joseph K. McKane
Attorney, Agent, or Firm—Keil & Weinkauf

[57] ABSTRACT

3-Isoxazolylbenzyl esters of the general formulae Ia and Ib

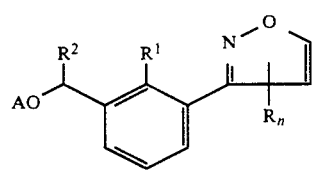

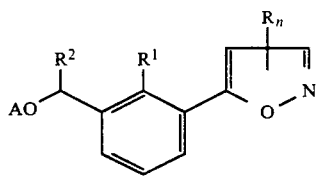

where
R is halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkenyl, $C_2$–$C_4$-haloalkenyl, $C_2$–$C_4$-alkynyl, $C_2$–$C_4$-haloalkynyl, unsubstituted or substituted phenylethenyl, $C_3$–$C_8$-cycloalkyl, aryl, hetaryl, $CO_2R^3$ or $CONR^4R^5$,
$R^3$, $R^4$ and $R^5$ are each hydrogen or $C_1$–$C_6$-alkyl,
n is 0, 1 or 2, and the radicals R may be different when n is 2,
$R^1$ is halogen or $C_1$–$C_4$-alkyl,
$R^2$ is hydrogen, $C_1$–$C_4$-alkyl, $C_2$–$C_4$-alkenyl, $C_2$–$C_4$-alkynyl or cyano and
A is the carbonyl radical of an acid component usually found in pyrethroids, are contained in pesticides.

7 Claims, No Drawings

3-ISOXAZOLYLBENZYL ESTERS, THEIR PREPARATION AND THEIR USE

The present invention relates to novel 3-isoxazolyl-benzyl esters of the general formulae Ia and Ib

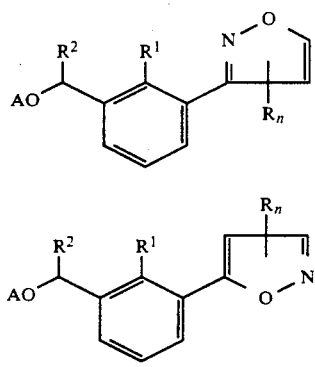

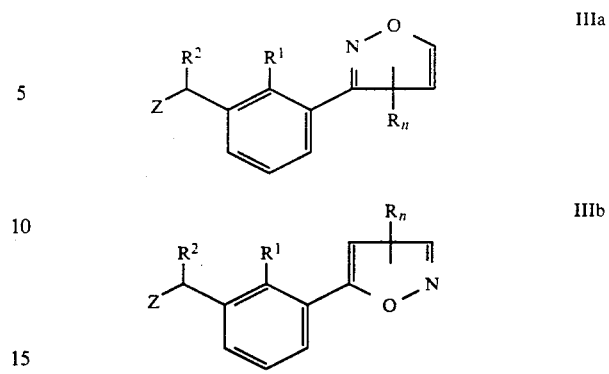

where
R is halogen, $C_1$–$C_4$-alkyl, $C_1C_4$-haloalkyl, $C_1$–$C_4$-alkoxy, $C_1$–$C_4$-haloalkoxy, $C_2$–$C_4$-alkenyl or $C_2$–$C_4$-haloalkenyl or is phenylethenyl which may carry from one to five halogen atoms, or is $C_2$–$C_4$-alkynyl, $C_3$–$C_8$-cycloalkyl, aryl, het aryl, $CO_2R^3$ or $CONR^4R^5$,
$R^3$, $R^4$ and $R^5$ are each hydrogen or $C_1$–$C_8$-alkyl,
n is 0, 1 or 2, and the radicals R may be different when n is 2,
$R^1$ is halogen or $C_1$–$C_4$-alkyl,
$R^2$ is hydrogen, $C_1$–$C_4$-alkyl, $C_2$–$C_4$-alkenyl, $C_2$–$C_4$-alkynyl or cyano and
A is the carbonyl radical of an acid component usually found in pyrethroids.

The present invention furthermore relates to 3-isoxazolylbenzyl derivatives of the general formulae IIIa and IIIb where R, $R^1$, $R^2$ and n have the abovementioned meanings and Z is hydroxyl or halogen.

It is known that certain benzyl esters having meta heteroaromatic structures (e.g. pyyrrolylbenzyl esters, 3-furanylbenzyl esters or 3-thienylbenzyl esters) have insecticidal or acaricidal activities (PCT Int. Appl. WO 82/1368; U.S. Pat. No. 4,426,524; J. Agric. Food Chem. 32 (1984), 1116; European Patent 110,769). However, the insecticidal or acaricidal activity of these esters is unsatisfactory at low application rates.

It is an object of the present invention to provide novel 3-hetarylbenzyl esters having improved properties with regard to the biological activity.

We have found that these objects are achieved by the 3-isoxazolylbenzyl esters Ia and Ib defined at the outset.

We have also found the novel intermediates IIIa and IIIb, processes for the preparation of the compounds Ia, Ib, IIIa and IIIb and the use of the compounds Ia and Ib for controlling pests.

The compounds Ia and Ib are obtained by reacting a 3-isoxazolylbenzyl alcohol or a corresponding benzyl halide of the formula IIIa or IIIb in a conventional manner with a carboxylic acid A-OH usually found in pyrethroids, or a derivative of said carboxylic acid.

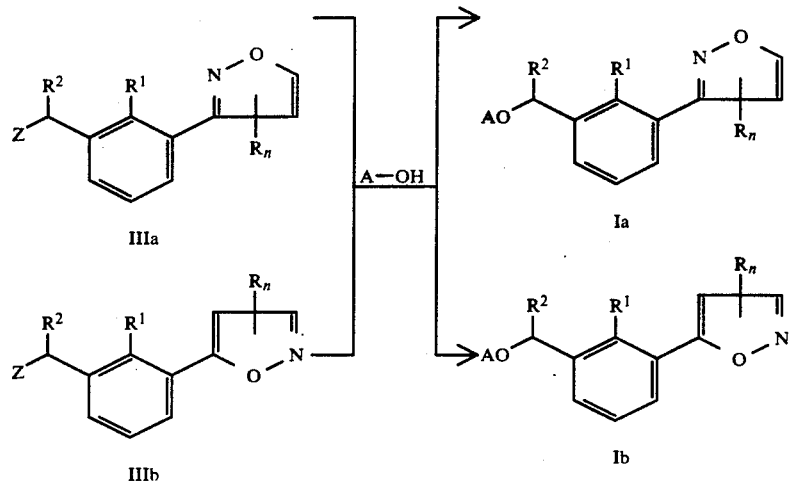

Suitable radicals Z are hydroxyl or halogen, in particular chlorine or bromine. Instead of the pyrethroid acid, the activated acid derivatives, such as anhydrides, halides, eg. chlorides or bromides, or imidazolides, may also be used.

The solvents used for this reaction are organic solvents, such as aliphatic and aromatic hydrocarbons and chlorohydrocarbons, e.g. petroleum ether, benzene, toluene, xylene, gasoline, dichloromethane, chloroform, tetrachloromethane, 1,2-dichloroethane or chlorobenzene, ethers, such as diethyl ether, di-n-butyl ether, methyl tert-butyl ether, tetrahydrofuran, dioxane, ketones, e.g. acetone, methyl ethyl ketone or methyl isopropyl ketone, and nitriles, such as acetonitrile and propionitrile, and corresponding mixtures.

Depending on which of the generally known processes is used for carrying out the esterification, it may be advisable to add a base or a reaction accelerator or to use conventional bases as a solvent (cf. Houben-Weyl, Methoden der organischen Chemie, Volume VIII, page 541 et seq., Georg-Thieme-Verlag, Stuttgart 1952).

Suitable acid acceptors are the conventional basic media, in particular aliphatic, aromatic and heterocyclic amines, e.g. triethylamine, dimethylamine, piperidine, dimethylaniline, dimethylbenzylamine, pyridine and 2-picoline.

The base is generally used in an excess of up to 5.0, preferably up to 2.0, in particular from 1.1 to 1.35, mole equivalents, based on the halide of the pyrethroid acid or the benzyl halide.

The reaction usually takes place at a sufficient rate at above 0° C. Since it generally occurs with evolution of heat, it may be advantageous to provide a means of cooling.

As a rule, the reaction is carried out at from $-40°$ to $140°$ C., preferably from $0°$ to $100°$ C., in particular from $10°$ to $50°$ C.

The reaction can be accelerated in a conventional manner by adding a catalyst, such as sulfuric acid, a hydrogen halide, a sulfonic acid or an acidic ion exchanger, and the equilibrium of the esterification can be shifted in the desired direction by removing the water or the ester I from the reaction mixture, for example by azeotropic distillation or by binding the water in sulfuric or hydrohalic acid.

In general, the 3-isoxazolylbenzyl alcohol derivatives IIIa or IIIb and the pyrethroid acids A—OH or their derivatives are reacted with one another in equimolar amounts. It may be advantageous for the yield to use the benzyl derivative in an excess or in less than the stoichiometric amount, based on the acid A-OH or its derivative.

In some cases, it is reasonable and advantageous to esterify the compounds of the formulae IIIa and IIIb in situ, particularly when $R^2$ in the general formulae IIIa and IIIb is cyano.

The novel esters can furthermore be prepared by virtually all known processes of ester synthesis, for example by reacting corresponding anhydrides with the alcohols of the formulae IIIa and IIIb, by reacting corresponding salts with derivatives of the alcohols of formulae IIIa and IIIb, for example the corresponding benzyl bromides or benzyl chlorides, or by transesterification (cf. Houben-Weyl loc. cit., pages 508–628).

Of course, the compounds of the formulae Ia and Ib occur in every case in the form of pure enantiomers or diastereomers and in many cases also in the form of mixtures of the structural isomers and can be used as active ingredients which occur in pure form or as mixtures, depending on the starting materials and the reaction conditions. The mixtures can be separated into their sterically pure components in a conventional manner; their biological activity is dependent on their steric configuration in specific cases.

The pyrethroid acids used and their derivatives are described in, for example, Wegler, Chemie der Pflanzenschutz- und Schädlingsbekämpfungsmittel, Volume VII, Springer Verlag, Berlin, Heidelberg, New York, 1981.

The 3-isoxazolylbenzyl derivatives IIIa and IIIb required for the preparation of the compounds Ia and Ib are obtainable by various methods.

For example, the compounds IIIa are obtained by converting a protected 3-formylbenzyl alcohol of the general formula IV into the corresponding oxime Va in a conventional manner in an inert organic solvent, in general in the presence of a base, then subjecting Va to an addition reaction with an alkyne of the formula VIa in an inert organic solvent in the presence of an oxidizing agent and of a base and cleaving off the protective group from the resulting 3-isoxazolylbenzyl ether VIIa in a conventional manner in an inert organic solvent in the presence of an acid or of a catalyst.

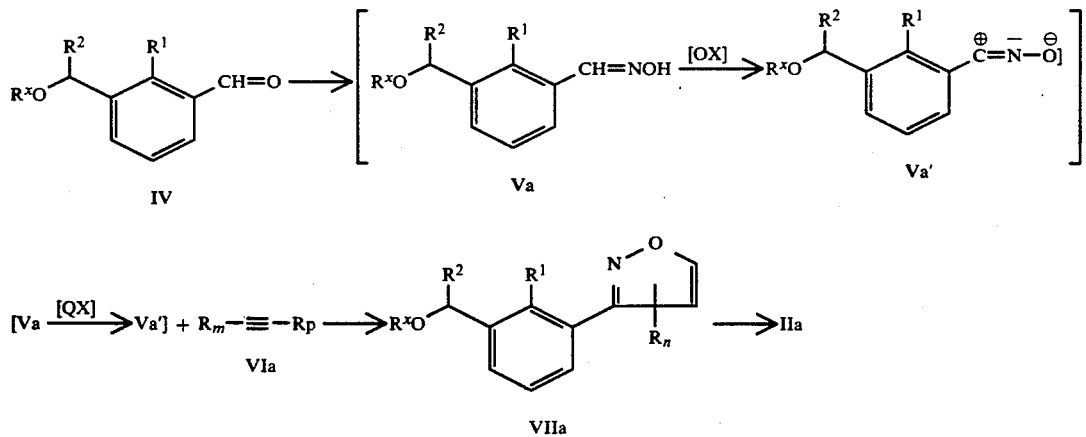

In formulae IV, Va, Va' and VIIa, $R^x$ is a protective group, such as methoxymethyl, 2-methoxyethoxymethyl, tetrahydro-2-pyranyl, tetrahydro-2-furanyl, tert-butyldimethylsilyl or trimethylsilyl.

m and p in formula VIa are each 0 or 1, the sum m+p corresponding to the value of n.

The conversion of the aldehyde IV into the oxime Va is carried out in a conventional manner (Houben-Weyl, Methoden der organischen Chemie, Vol. VII/1, page 471 et seq., and Vol. X/4, page 56 et seq.).

The subsequent cleavage of the 3-isoxazolylbenzyl ether VIIa to give the 3-isoxazolylbenzyl alcohol is carried out in a conventional manner (T. Greene, Protective Groups in Organic Chemistry, J. Wiley & Sons, New York 1981; Tietze et al., Reaktionen und Synthesen, Georg-Thieme-Verlag 1981, page 363 et seq.) in an inert organic solvent in the presence of an acid or of a catalyst.

The 3-isoxazolylbenzyl alcohols IIIb are obtained in a similar manner by converting an ether-protected 3-formylbenzyl alcohol of the general formula IV into the corresponding 3-bromovinyl derivative VIII in a conventional manner by a Wittig or Horner-Wittig reaction in an inert organic solvent in the presence of a base by means of a phosphonium or phosphonate reagent, then converting VIII into an alkyne of the formula VIb in an inert organic solvent in the presence of a base, thereafter subjecting said alkyne to an addition reaction with an oxime of the formula Vb in a conventional manner in an inert organic solvent in the presence of an oxidizing agent and of a base to give the 3-isoxazolylbenzyl ether VIIb, from which the protective group is cleaved off in a conventional manner.

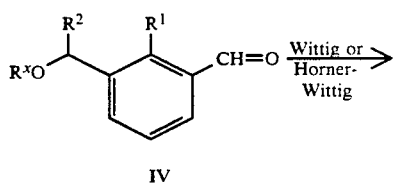

IV

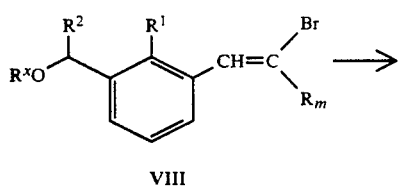

VIII

VIb

VIb + $R_p$—CH=NOH ⟶
Vb

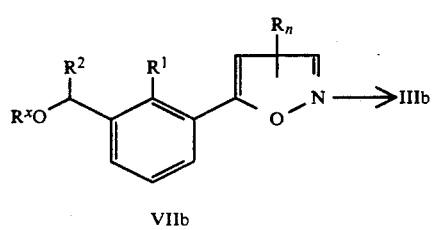

VIIb

Preferred Wittig or Horner-Wittig reagents are the triphenylphosphonium halides and the diethyl phosphonates.

The radicals $R^x$ (formula IV, IX, VIb and VIIb), $R_m$ (formulae VIII, IX and VIb) and $R_p$ (formula Vb) have the abovementioned meanings.

The Wittig or Horner-Wittig reaction of the aldehyde IV is carried out in a conventional manner (e.g. Liebigs Ann. Chem., 1980, page 2061 et seq.; Synthesis 1975, page 458 et seq.; DE-A 3 927 479).

The reaction of Vb with VIb and the corresponding cleavage of the ether VIIb are carried out under conditions similar to those described above for the reaction of Va with VIa and the cleavage of the ether VIIa.

The following reactions known from the literature are also particularly suitable for the preparation of the 3-isoxazolylbenzyl alcohols IIIb in which n is 0 or 1:

1. Similarly to Tietze et al., Reaktionen and Synthesen, Georg-Thieme-Verlag, 1981, page 299 et seq.

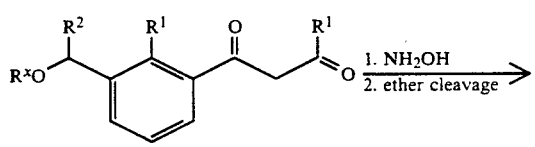

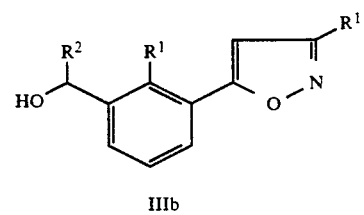

IIIb

2. Similarly to Huisgen et al., Chem. Ber. 1973, page 3291 et seq.

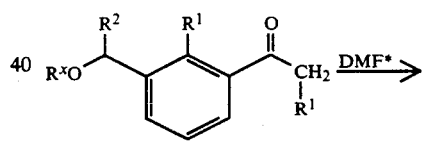

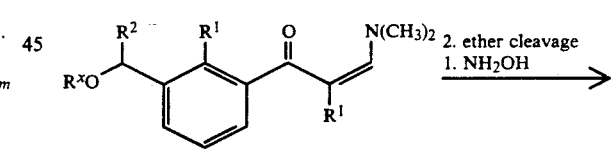

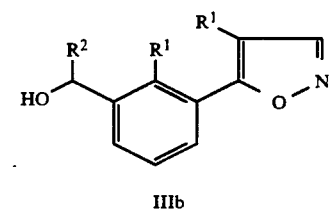

IIIb

3. Similarly to Bowden et al., J. Chem. Soc. 1946, 953 et seq.

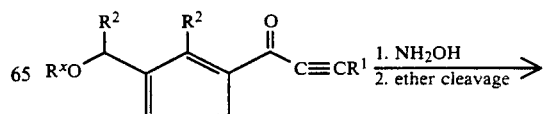

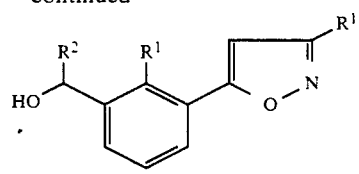

The 3-formylbenzyl ether IV required for the synthesis of the 3-isoxazolylbenzyl alcohols IIIa and IIIb is prepared by conventional methods (DE-A 3 927 479) in accordance with the following reaction scheme:

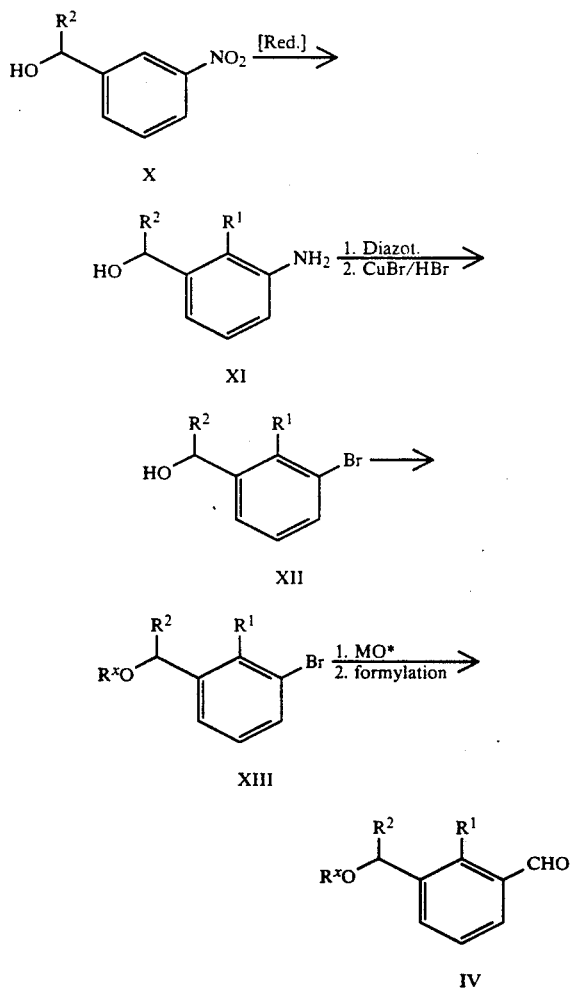

The reduction of X to XI and the diazotization of XI to XII can be carried out by processes described in EP-A 54 180.

The alcohol XII can be converted into the ether XIII by the method described in Tietze/Eicher (Reaktionen und Synthesen, Thieme Verlag, 1981, page 184).

A suitable reaction for the preparation of the aldehyde IV is the reaction of the corresponding organometallic compounds (Grignard compound or organolithium compound) with certain formamides, e.g. dimethylformamide, 1-formylpiperidine or 2-(formylmethylamino)-pyridine (cf. Houben-Weyl, Methoden der organischen Chemie, Volume E 3, page 130).

The benzyl alcohols of the general formula III, where $R^2$ is cyano, $C_2$-$C_4$-alkynyl, $C_2$-$C_4$-alkenyl or $C_1$-$C_4$-alkyl, are advantageously obtained by first oxidizing the unsubstituted benzyl alcohols in which $R^2$ is H to the corresponding benzaldehydes IX.

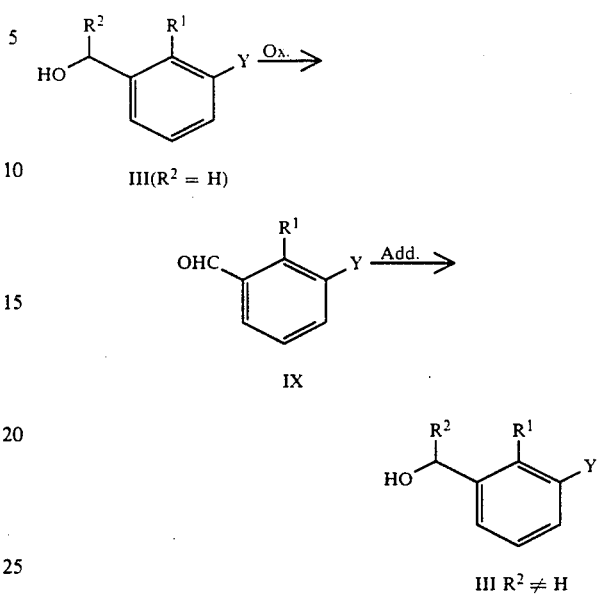

In formulae III and XIV, Z is the isoxazolyl radical in this case. Suitable oxidizing agents are all conventional oxidizing agents which convert primary alcohols into aldehydes (Houben-Weyl, Methoden der organischen Chemie, Volume E3, page 265 et seq.). Compounds containing transition metals in a higher oxidation state, for example pyridinium chlorochromate, are particularly suitable.

The benzaldehydes IX can be converted into the substituted benzyl alcohols in which $RH^2 \neq H$ in a subsequent reaction step in a conventional manner.

a) Where $R^2$ is CN, the benzaldehyde is reacted with hydrocyanic acid or a metal cyanide in the presence or absence of an acid;

b) Where $R^2$ is $C_2$-$C_4$-alkynyl, $C_2$-$C_4$-alkenyl or $C_1$-$C_4$-alkyl, the benzaldehyde is reacted with an organometallic compound $MR^2$ or $R^2Hal$, where M is an alkali metal, alkaline earth metal or transition metal and Hal is halogen.

For the preparation of the cyanohydrins, the benzaldehydes are reacted with hydrocyanic acid, with hydrocyanic acid produced in situ from metal cyanides or with metal cyanides in the presence of an alkali metal bisulfite solution, if necessary basic catalysts, such as potassium carbonate, or phase transfer catalysts, eg. benzyltriethylammonium chloride being added. Preferably used metal cyanides are alkali metal cyanides, e.g. sodium cyanide or potassium cyanide.

The reaction is carried out in a conventional manner, for example as described in Houben-Weyl, Methoden der organischen Chemie, Volume VIII, pages 274–278, 1952 Edition, and Volume E5, page 1413 et seq., 1985.

Suitable organometallic compounds are the corresponding ones, in particular organolithium compounds $LiR^2$, such as methyllithium, ethyllithium, butyllithium, or the corresponding Grignard compounds $R^2Hal$, where Hal is chlorine, bromine or iodine, e.g. methylmagnesium bromide, ethylmagnesium bromide, propylmagnesium iodide or vinylmagnesium iodide.

The reaction with organometallic compounds can be carried out in a conventional manner, for example as described in Houben-Weyl, Methoden der organischen Chemie, Volume XIII/2a, page 285 et seq., 1973, in an inert organic solvent, such as ether or tetrahydrofuran, under a protective gas, so that no further information is required here.

In view of the intended use of the compounds Ia and Ib, examples of suitable substituents are the following radicals:

R is halogen, such as fluorine, chlorine, bromine or iodine;

alkyl, such as methyl, ethyl, propyl, 1-methylethyl, butyl, 1-methylpropyl, 2-methylpropyl or 1,1-dimethylethyl, preferably methyl or ethyl;

haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl;

alkoxy, such as methoxy, ethoxy, propoxy, 1-methylethoxy, butoxy, 1-methylpropoxy, 2-methylpropoxy or 1,1-dimethylethoxy;

haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy;

alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl or 2-methyl 2-propenyl;

haloalkenyl, such as 2,2-dichloroethenyl, 2,2-dibromomethenyl, 2,2-difluoroethenyl, 2-chloro-2-fluoroethenyl, 2-bromo-2-chloroethenyl, 2-bromo-2-fluoroethenyl, 2,2-di(trifluoromethyl)-ethenyl, 2-chloro-2-trifluoromethylethenyl or 2-fluoro-2-trifluoromethylethenyl;

phenylethenyl which may carry from one to five halogen atoms, in particular fluorine or chlorine, both on the phenyl ring and on the ethenyl group, in particular 2-chloro-2-(4-chlorophenyl)-ethenyl;

alkynyl, such as ethynyl, 1-propynyl, 2-propynyl, 1-butynyl, 2-butynyl, 3-butynyl, or 1-methyl-2-propynyl;

cycloalkyl, such as cyclopropyl, cyclobutyl, cyclopentyl, cyclohexyl or cycloheptyl;

aryl, such as phenyl or naphthyl;

hetaryl, such as a 5-membered or a 6-membered heteroaromatic system, e.g. pyrrolyl, pyrazolyl, imidazolyl, isoxazolyl, oxazolyl, isothiazolyl, thiazolyl, furanyl, thienyl or pyridyl;

or a carboxylate group $CO_2R^3$ or a carboxamide group $CONR^4R^5$, $R^3$, $R^4$ and $R^5$ are each hydrogen or alkyl as stated above, or pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-butyl, 1,1,2-trimethylpropyl, 1,2,2-trimethylpropyl, 1-ethyl-1-methylpropyl and 1-ethyl-2-methylpropyl;

$R^3$, $R^4$ and $R^5$ are each preferably methyl or ethyl;

n is 0, 1 or 2, and the radicals R may be different when n is 2;

$R^1$ is halogen as stated for R, preferably fluorine or chlorine, or alkyl as stated for $R^4$, preferably methyl or ethyl, $R^2$ is hydrogen, alkyl as stated for R, alkenyl as stated for R, alkynyl as stated or R, preferably ethynyl or cyano and A is the carbonyl radical of an acid component usually found in pyrethroids.

Preferred carbonyl radicals A are the radicals of the formulae II.A and II.B

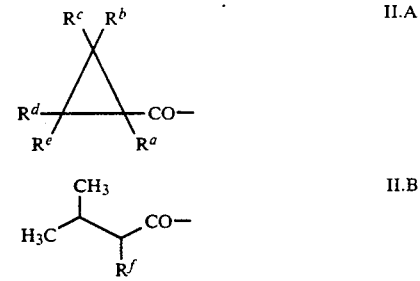

where
$R^a$ is hydrogen;
alkyl as stated for R or
phenyl which may carry from one to five halogen atoms as stated for R, preferably chlorine, in particular in the 4-position, and/or from one to three of the following radicals: alkyl as stated for R, haloalkyl as stated for R, alkoxy as stated for R, preferably ethoxy, in particular in the 4-position, or haloalkoxy as stated for R, or
alkylthio, such as methylthio, ethylthio, propylthio, 1-methylethylthio, butylthio, 1-methylpropylthio, 2-methylpropylthio or 1,1-dimethylethylthio;

$R^b$, $R^c$ and $R^d$ independently of one another are each hydrogen, halogen as stated for R, preferably chlorine or bromine, or alkyl as stated for R, preferably methyl;

$R^b$ is halogen or alkyl as stated for R, preferably chlorine, bromine or methyl;

$R^c$ is in general and in particular a radical stated for $R^b$;

$R^d$ is in particular hydrogen or methyl;

$R^e$ is hydrogen;

halogen as stated for R, preferably chlorine or bromine; alkyl as stated for R, preferably methyl;

haloalkyl as stated for R; alkenyl as stated for R or 1-pentenyl, 2-pentenyl, 3-pentenyl, 4-pentenyl, 1-methyl-1-butenyl 2-methyl-1-butenyl, 3-methyl-1-butenyl, 1-methyl-2-butenyl, 2methyl-2-butenyl, 3-methyl-2-butenyl, 1-methyl-3-butenyl, 2-methyl-3-butenyl, 3-methyl-3-butenyl, 1,1-dimethyl-2-propenyl, 1-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentynyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2- dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, preferably ethenyl, 1-propenyl or 1-methyl-1-propenyl which may carry from one to eight halogen atoms as stated for R, preferably fluorine, chlorine and/or bromine and/or one of the following radicals:

alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl, preferably methoxycarbonyl, or phenyl which may carry from one to five halogen atoms as stated for R and/or from one to three of the following radicals: alkyl as stated for R, preferably tert-butyl, haloalkyl as stated for R, alkoxy as stated for R, haloalkoxy as stated for R or alkylthio such as methylthio, ethylthio, propylthio, 1-methylethylthio, butylthio, 1-methylpropylthio, 2-methylpropylthio or 1,1-dimethylethylthio; or cycloalkylidenemethyl such as cyclopropylidenemethyl, cyclobutylidenemethyl, cyclopentylidenemethyl, cyclohexylidenemethyl or cycloheptylidenemethyl, preferably cyclopentylidenemethyl;

$R^f$ is a mononuclear or dinuclear aromatic or heteroaromatic ring system which may contain a nitrogen atom as a hetero atom;

phenyl which may carry from one to five halogen atoms as stated for R, preferably fluorine or chlorine, in particular in the 4-position, and/or from one to three of the following radicals: alkyl as stated for R, preferably 1,1-dimethylethyl, in particular in the 4-position, haloalkyl as stated for R, preferably difluoromethyl, alkoxy as stated for R, haloalkoxy as stated for R or alkylthio, such as methylthio, ethylthio, propylthio, 1-methylethylthio, butylthio, 1-methylpropylthio, 2-methylpropylthio or 1,1-dimethylethylthio, or phenylamino where the phenyl ring in turn may carry from one to five halogen atoms as stated for R, preferably fluorine or chlorine, in particular in the 2-position, and/or from one to three of the following radicals: alkyl as stated for R, preferably methyl, haloalkyl as stated for R, preferably trifluoromethyl, alkoxy as stated for R, preferably methoxy, haloalkoxy as stated for R, or alkylthio, such as methylthio, ethylthio, propylthio, 1-methylethylthio, butylthio, 1-methylpropylthio, 2-methylpropylthio or 1,1-dimethylethylthio.

Particularly preferred substituents A are the carbonyl radicals of the pyrethroid acids of formulae IIa and IIb, which are shown in the Tables below:

Pyrethroid acids of the general formula IIa $$\underset{R^e}{\overset{R^c}{\underset{R^d}{\triangle}}}\overset{R^b}{\underset{R^a}{-CO_2H}} \qquad \text{IIa}$$

| Formula No. | $R^a$ | $R^b$ | $R^c$ | $R^d$ | $R^e$ |
|---|---|---|---|---|---|
| A.001 | H | CH$_3$ | CH$_3$ | H | CH=C(CH$_3$)$_2$ |
| A.002 | H | CH$_3$ | CH$_3$ | H | CH=CCl$_2$ |
| A.003 | H | CH$_3$ | CH$_3$ | H | CH=CCl—CF$_3$ |
| A.004 | H | CH$_3$ | CH$_3$ | H | CH=CBr$_2$ |
| A.005 | H | CH$_3$ | CH$_3$ | H | CH=CF$_2$ |
| A.006 | H | CH$_3$ | CH$_3$ | H | CH=CF—CF$_3$ |
| A.007 | H | CH$_3$ | CH$_3$ | H | CH=C(CF$_3$)$_2$ |
| A.008 | H | CH$_3$ | CH$_3$ | CH$_3$ | CH$_3$ |
| A.009 | 4-Cl—C$_6$H$_4$ | H | H | H | H |
| A.010 | 4-OCH$_2$CH$_3$—C$_6$H$_4$ | Cl | Cl | H | H |
| A.011 | H | CH$_3$ | CH$_3$ | H | CH=CCl—(4-Cl—C$_6$H$_4$) |
| A.012 | H | CH$_3$ | CH$_3$ | H | CH=CH—CH=CH$_2$ |
| A.013 | H | CH$_3$ | CH$_3$ | H | CH=C(CH$_3$)—CO$_2$CH$_3$ |
| A.014 | H | CH$_3$ | CH$_3$ | H | CH=CH—(2-phenyl) * |
| A.015 | H | CH$_3$ | CH$_3$ | H | Cyclopentylidenemethyl |
| A.016 | H | CH$_3$ | CH$_3$ | H | CHBr—CBrCl$_2$ |
| A.017 | H | CH$_3$ | CH$_3$ | H | 4-(CH$_3$)$_3$C—C$_6$H$_4$ |

*2,2H-Indenespiro group

Pyrethroid acids of the general formula IIb $$\underset{R^f}{\overset{CH_3}{H_3C}}\overset{}{\diagdown}CO_2H \qquad \text{IIb}$$

| Formula No. | $R^f$ |
|---|---|
| B.001 | 4-Cl—C$_6$H$_4$ |
| B.002 | 4-F—C$_6$H$_4$ |
| B.003 | 4-OCHF$_2$—C$_6$H$_4$ |

-continued

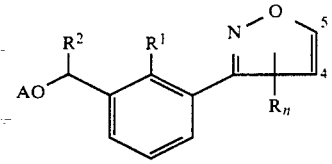

| Formula No. | $R^f$ |
|---|---|
| B.004 | NH—(2-Cl,4-CF$_3$—C$_6$H$_3$) |
| B.005 | NH—(2-F,4-CF$_3$—C$_6$H$_3$) |
| B.006 | NH—(4-CF$_3$—C$_6$H$_3$) |
| B.007 | 1-Pyrrolyl |
| B.008 | 3-CH$_3$-1-Pyrrolyl |
| B.009 | 3,4-(CH$_3$)$_2$-1-pyrrolyl |
| B.010 | 2,5-(CH$_3$)$_2$-1-pyrrolyl |
| B.011 | 2-Isoindolyl |

In view of their biological activity, 3-isoxazolylbenzyl esters of the general formulae Ia and Ib in which $R^1$ is methyl or ethyl and $R^2$ is hydrogen are preferred for pest control.

3-Isoxazolylbenzyl esters of the general formulae Ia and Ib in which $R^1$ is methyl or ethyl and $R^2$ is hydrogen and n is 0 are also preferred.

3-Isoxazolylbenzyl esters Ia and Ib in which A is a carbonyl radical of a pyrethroid acid of the general formula IIa, where $R^a$ and $R^d$ are each hydrogen, $R^b$ and $R^c$ are each methyl and $R^e$ is C$_2$–C$_4$-alkenyl which carries from two to six halogen atoms, are particularly preferred.

3-Isoxazolylbenzyl esters Ia and Ib in which A is the carbonyl radical of the pyrethroid acid A.002, A.003 or A.005 are very particularly preferred.

Examples of particularly active compounds Ia and Ib are shown in Tables A and B below, where the radical A is characterized by the formula No. of the corresponding acid.

TABLE A

| A | $R^1$ | $R^2$ | $R_n$ |
|---|---|---|---|
| A.001 | CH$_3$ | H | — |
| A.002 | CH$_3$ | H | — |
| A.004 | CH$_3$ | H | — |
| A.005 | CH$_3$ | H | — |
| B.001 | CH$_3$ | H | — |
| B.005 | CH$_3$ | H | — |
| A.001 | CH$_3$ | CN | — |
| A.002 | CH$_3$ | CN | — |
| A.003 | CH$_3$ | CN | — |
| A.004 | CH$_3$ | CN | — |
| A.005 | CH$_3$ | CN | — |
| B.001 | CH$_3$ | CN | — |
| B.005 | CH$_3$ | CN | — |
| A.001 | CH$_3$ | C≡CH | — |
| A.002 | CH$_3$ | C≡CH | — |
| A.003 | CH$_3$ | C≡CH | — |
| A.004 | CH$_3$ | C≡CH | — |
| A.005 | CH$_3$ | C≡CH | — |
| B.001 | CH$_3$ | C≡CH | — |
| B.005 | CH$_3$ | C≡CH | — |
| A.001 | CH$_3$ | H | 5-COOCH$_3$ |
| A.002 | CH$_3$ | H | 5-COOCH$_3$ |
| A.003 | CH$_3$ | H | 5-COOCH$_3$ |
| A.004 | CH$_3$ | H | 5-COOCH$_3$ |
| A.005 | CH$_3$ | H | 5-COOCH$_3$ |
| B.001 | CH$_3$ | H | 5-COOCH$_3$ |

TABLE A-continued

| A | $R^1$ | $R^2$ | $R_n$ |
|---|---|---|---|
| B.005 | CH$_3$ | H | 5-COOCH$_3$ |
| A.001 | CH$_3$ | CN | 5-COOCH$_3$ |
| A.002 | CH$_3$ | CN | 5-COOCH$_3$ |
| A.003 | CH$_3$ | CN | 5-COOCH$_3$ |
| A.004 | CH$_3$ | CN | 5-COOCH$_3$ |
| A.005 | CH$_3$ | CN | 5-COOCH$_3$ |
| B.001 | CH$_3$ | CN | 5-COOCH$_3$ |
| B.005 | CH$_3$ | CN | 5-COOCH$_3$ |
| A.001 | CH$_3$ | C≡CH | 5-COOCH$_3$ |
| B.002 | CH$_3$ | C≡CH | 5-COOCH$_3$ |
| A.003 | CH$_3$ | C≡CH | 5-COOCH$_3$ |
| A.004 | CH$_3$ | C≡CH | 5-COOCH$_3$ |
| A.005 | CH$_3$ | C≡CH | 5-COOCH$_3$ |
| B.001 | CH$_3$ | C≡CH | 5-COOCH$_3$ |
| B.005 | CH$_3$ | C≡CH | 5-COOCH$_3$ |

TABLE B

| A | $R^1$ | $R^2$ | $R_n$ |
|---|---|---|---|
| A.001 | CH$_3$ | H | 3-CH$_2$CH$_3$ |
| A.002 | CH$_3$ | H | 3-CH$_2$CH$_3$ |
| A.003 | CH$_3$ | H | 3-CH$_2$CH$_3$ |
| A.004 | CH$_3$ | H | 3-CH$_2$CH$_3$ |
| A.005 | CH$_3$ | H | 3-CH$_2$CH$_3$ |
| B.001 | CH$_3$ | H | 3-CH$_2$CH$_3$ |
| A.005 | CH$_3$ | H | 3-CH$_2$CH$_3$ |
| A.001 | CH$_3$ | H | 3-CH$_3$ |
| A.002 | CH$_3$ | H | 3-CH$_3$ |
| A.003 | CH$_3$ | H | 3-CH$_3$ |
| A.004 | CH$_3$ | H | 3-CH$_3$ |
| A.005 | CH$_3$ | H | 3-CH$_3$ |
| B.001 | CH$_3$ | H | 3-CH$_3$ |
| A.005 | CH$_3$ | H | 3-CH$_3$ |
| A.001 | CH$_3$ | H | — |
| A.002 | CH$_3$ | H | — |
| A.003 | CH$_3$ | H | — |
| A.004 | CH$_3$ | H | — |
| A.005 | CH$_3$ | H | — |
| B.001 | CH$_3$ | H | — |
| A.005 | CH$_3$ | H | — |

The 3-isoxazolylbenzyl esters of the formula Ia and Ib are suitable for effectively controlling pests from the class consisting of the insects, arachnids and nematodes. They can be used as pesticides in crop protection and in the hygiene and veterinary sectors and for the protection of stored material.

The insect example include, from the order of the butterflies (Lepidoptera), for example Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia

*ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panoli flamea, Pectinophora gossypiella, Peridroma saucia, Phalera bucephala, Phthorimaea operculella, Phyllocnistis citrella, Pieris brassicae, Plathypena scarbra, Plutella xylostella, Psuedoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* from the order of the beetles (*Coleoptera*), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyl lophaga sp., Phyllopertha horticola, Phyllotreta nemorum, Phyllotreta strilata, Popillia japonica, Sitona lineatus* and *Sitophilus granaria;* from the order of the *Diptera*, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilla sericata, Lycoria pectoralis, Mayetiola destructor, Musca domestica, Muscina stabulans, Oesbrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* from the order of the *Thysanoptera*, for example *Frankliniella fusca, Frankliniella occidentalis, Frankliniella tritici, Scirtothrips citri, Thrips oryzae, Thrips palmi* and *Thrips tabaci;* from the order of the *Hymenoptera*, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta;* from the order of the *Heteroptera*, for example *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor;* from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulocorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii;* from the order of the *Isoptera*, for example *Calotermes flavicollis, Leucotermes flavipens, Reticuliterm lucifugus* and *Terms natalensis;* from the order of the *Orthoptera*, for example *Acheta domestica, Blatta orientalis, Blatella germanica, Forficula auricularia, Gryllotalpa gryllotalpa, Locusta migratoria, Melanoplus birittatus, Melanoplus femurrubrum, Melanoplus mexicanus, Melanoplus sanguinipes Melanoplus spretus, Nomadacris septemfasciata, Periplaneta americana, Schistocerca americana, Schistocerca peregrina, Stauronotus maroccanus* and *Tachycines asynamorus;* from the class of the *Arachnoidea*, for example *Acarina*, such as *Amblyomma americanum, Amblyomma variegatum, Argas persicus, Boophilus annulatus, Boophilus decolaratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanazawai, Tetranychus pacificus, Tetranychus telarius* and *Tetranychus urticae;* from the class of the *nematodes*, for example root gall nematodes, e.g. *Meloidogyne hapla, Meloidgyne incognita* and *Meloidgyne javanica*, cyst-forming nematodes, e.g. *Globodera rostochiensis, Heterodera avenae, Heterodera glycinae, Heterodera schatii, Heterodera trifolii,* and stem and leaf borers, e.g. *Belonolaimus lonicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients can be used as such, in the form of their formulations or in the application forms prepared therefrom, for example in the form of directly sprayable solutions, powders, suspensions or dispersions, emulsions, oil dispersions, pastes, dusting agents, broadcasting agents or granules, by spraying, atomizing, dusting, broadcasting or pouring. The application forms depend entirely on the intended uses; they should in any case ensure very fine distribution of the novel active ingredients.

For the preparation of directly sprayable solutions, emulsions, pastes or oil dispersions, mineral oil fractions having a medium to high boiling point, such as kerosene or diesel oil, coal tar oils and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone or strongly polar solvents, e.g. dimethylformamide, dimethyl sulfoxide, N-methylpyrrolidone or water, are suitable.

Aqueous application forms can be prepared from emulsion concentrates, pastes or wettable powders (spray powders or oil dispersions) by adding water. For the preparation of emulsions, pastes or oil dispersions, the substances, as such or in solution in an oil or solvent, can be homogenized in water by means of wetting agents, adhesives, dispersants or emulsifiers. However, it is also possible to prepare concentrates which consist of active substance, wetting agents, adhesives, dispersants and emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and alkali metal and alkaline earth metal salts thereof, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusting agents can be prepared by mixing or milling the active substances together with a solid carrier.

The formulations contain in general from 0.01 to 95, preferably from 0.1 to 90, % by weight of the active ingredient. The active ingredients are used in a purity of from 90 to 100%, preferably from 95 to 100% (according to the NMR spectrum).

Examples of formulations are:

I. 5 parts by weight of compound No. 2.001 are thoroughly mixed with 95 parts by weight of finely divided kaolin. A dusting agent which contains 5% by weight of the active ingredient is obtained in this manner.

II. 30 parts by weight of compound No. 1.003 are thoroughly mixed with a mixture of 92 parts by weight of silica gel powder and 8 parts by weight of liquid paraffin, which was sprayed onto the surface of the silica gel. A formulation of the active ingredient having good adhesion and containing 23% by weight of active ingredient is obtained in this manner.

III. 10 parts by weight of compound No. 1.002 are dissolved in a mixture which consists of 90 parts by weight of xylene, 6 parts by weight of the adduct of from 8 to 10 moles of ethylene oxide with 1 mole of oleic acid N-monoethanolamide, 2 parts by weight of the calcium salt of dodecylbenzenesulfonic acid and 2 parts by weight of the adduct of 40 moles of ethylene oxide and 1 mole of castor oil (active ingredient content 9% by weight).

IV. 20 parts by weight of compound No. 1.005 are dissolved in a mixture which consists of 60 parts by weight of cyclohexanone, 30 parts by weight of isobutanol, 5 parts by weight of the adduct of 7 moles of ethylene oxide with 1 mole of isooctylphenol and 5 parts by weight of the adduct of 40 moles of ethylene oxide with 1 mole of castor oil (active ingredient content 16% by weight).

V. 80 parts by weight of compound No. 1.001 are thoroughly mixed with 3 parts by weight of the sodium salt of diisobutylnaphthalene-alphasulfonic acid, 10 parts by weight of the sodium salt of a ligninsulfonic acid obtained from a sulfite waste liquor and 7 parts by weight of silica gel powder, and the mixture is milled in a hammer mill (active ingredient content 80% by weight).

VI. 90 parts by weight of compound No. 1.004 are mixed with 10 parts by weight of N-methyl-α-pyrrolidone, and a solution which is suitable for use in the form of very small drops is obtained (active ingredient content 90% by weight).

VII. 20 parts by weight of compound No. 1.001 are dissolved in a mixture which consists of 40 parts by weight of cyclohexanone, 30 parts by weight of isobutanol, 20 parts by weight of the adduct of 7 moles of ethylene oxide and 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

VIII. 20 parts by weight of active ingredient No. 2.001 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

Granules, for example coated, impregnated and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, e.g. ammonium sulfate, ammonium phosphate, ammonium nitrate or ureas, and vegetable products, such as cereal meal, ground bark, woodmeal and nutshell meal, cellulose powder and other solid carriers.

The active ingredient concentrations in the ready-to-use formulations can be varied within wide ranges.

In general, they are from 0.0001 to 10%, preferably from 0.01 to 1%.

The active ingredients can also be successfully used in the ultra low volume method (ULV), and it is possible to apply formulations containing more than 95% by weight of active ingredient or even the active ingredient without additives.

The application rate of active ingredient under open air conditions is from 0.01 to 10, preferably from 0.1 to 1, kg/ha.

Oils of various types, herbicides, fungicides, other pesticides and bactericides, can be added to the active ingredients, if necessary directly before use (tank mix). These agents can be mixed with the novel agents in a weight ratio of from 1:10 to 10:1.

SYNTHESIS EXAMPLES

The methods described in the Synthesis Examples below were used, with appropriate modification of the starting compounds, to obtain further compounds Ia and Ib. The compounds thus obtained are shown in the Tables below, together with physical data.

Preparation of starting materials

1. 3-Amino-2-methylbenzyl alcohol

A solution of 203 g of 2-methyl-3-nitrobenzyl alcohol in 1,000 ml of ethanol is hydrogenated in the presence of 5 g of 10% strength Pd/carbon at from 30° to 35° C. The catalyst is filtered off, the solution is evaporated down and the resulting solid is dried. 145 g of 3-amino-2-methylbenzyl alcohol of melting point 104°-108° C. are obtained.

2. 3-Bromo-2-methylbenzyl alcohol

A solution of 40.7 g of sodium nitrate in 300 ml of water is added dropwise to a mixture cooled to 0° C. and consisting of 888 ml of water, 162 ml of 47% strength hydrobromic acid and 81.2 g of 3-amino-2-methylbenzyl alcohol. Stirring is carried out for 30 minutes at 0° C., after which a suspension of 168.7 g of copper(I) bromide in 750 ml of water is added a little at a time at this temperature. The reaction mixture is stirred in succession for 1 hour at 10° C, for 1 hour at room temperature and for 2 hours at 100° C. After cooling, the reaction mixture is extracted several times with ether. The combined organic phases are washed with water, dried and evaporated down. After purification by column chromatography over silica gel using toluene as the mobile phase, 64.2 g of 3-bromo-2-methylbenzyl alcohol of melting point 97°-100° C. are obtained.

3-Bromo-2-methylbenzyl tetrahydro-2-pyranyl ether 2.1 ml of concentrated hydrochloric acid are added at 0° C. to a solution of 208.9 g of 3-bromo-2-methylbenzyl alcohol and 87.4 g of 3,4-dihydro-2H-pyran in 1,600 ml of ether. Stirring is carried out for 4 days at room temperature, after which 50 ml of 10% strength potassium hydroxide solution and 500 ml of water are added dropwise. The organic phase is separated off, the aqueous phase is extracted with ether and the combined organic phases are washed with water, dried and evaporated down. After purification by column chromatography over silica gel using toluene as the mobile phase, 224.6 g of the desired compound are obtained.

NMR spectrum [300 MHz; $CDCl_3$; δ(ppm)]: 1.4–1.91 (6H); 2.42 (3H); 3.55 (1H); 3.89 (1H); 4.47 (1H); 4.68 (1H); 4.8 (1H); 7.02 (1H); 7.32 (1H); 7.47 (1H).

4. 3-Formyl-2-methylbenzyl tetrahydro-2-pyranyl ether 1.2 g of Mg (magnesium turnings) in 15 ml of absolute tetrahydrofuran are initially taken under a nitrogen atmosphere. A few drops of dibromoethane are added at 65° C. A solution of 14.25 g of 3-bromo-2-methylbenzyl tetrahydro-2-pyranyl ether in 50 ml of tetrahydrofuran is added dropwise while the temperature is kept at 65° C. The stirred mixture is then refluxed for 2 hours. A solution of 5.65 g of N-formylpiperidine in 10 ml of absolute tetrahydrofuran is added dropwise to the reaction mixture, which has been cooled to 0° C. Stirring is carried out for 20 hours at room temperature and the mixture is rendered slightly acidic with about 50 ml of 5% strength hydrochloric acid and is extracted several times with ether. The combined ether extracts are washed with water, dried and evaporated down. The crude product (11 g) can be purified by column chromatography over silica gel using 97.5:2.5 toluene/acetone.

NMR spectrum [250 MHz; $CDCl_3$; δ(ppm)]: 1.48–1.93 (6H); 2.64 (3H); 3.57 (1H); 3.9 (1H); 4.54 (1H); 4.72 (1H); 4.86 (1H); 7.36 (1H); 7.65 (1H); 7.76 (1H); 10.33 (1H).

5. 3-(2',2'-Dibromovinyl)-2-methylbenzyl tetrahydro-2-pyranyl ether

A solution of 41.44 g of tetrabromomethane in 40 ml of methylene chloride is added dropwise at 0° C. to a solution of 64.85 g of triphenylphosphine in 60 ml of methylene chloride. Stirring is carried out for 30 minutes at 0° C., after which 23.1 g of 3-formyl-2-methylbenzyl tetrahydro-2-pyranyl ether in 25 ml of methylene chloride are added dropwise. Stirring is carried out for 2 hours at room temperature, after which the solid is filtered off and the filtrate is evaporated down. 200 ml of cyclohexane and 200 ml of water are added to the filtrate. The stirred mixture is refluxed for 1 hour and the organic phase is separated off, dried and evaporated down. After purification by column chromatography over silica gel using cyclohexane and toluene as the mobile phase, 18.4 g of the desired compound are obtained, in addition to 4 g of 3-(2',2'-dibromovinyl)-2-methylbenzyl bromide.

NMR spectrum [300 MHz; $CDCl_3$; δ(ppm)]: 1.48–1.92 (6H); 2.23 (3H); 3.55 (1H); 3.9 (1H); 4.48 (1H); 4.72 (1H); 4.81 (1H); 7.19 (1H); 7.28 (1H); 7.38 (1H); 7.5 (1H).

6. 3-(2',2'-Dichlorovinyl)-2-methylbenzyl tetrahydro-2-pyranyl ether

Method A 7.86 g of triphenylphosphine are added rapidly at 0°-5° C. to a suspension of 3.37 g of potassium tert-butylate in 50 ml of heptane under a nitrogen atmosphere. 3.59 g of chloroform in 30 ml of heptane are then added dropwise in the course of 1 hour, likewise at 0°-5° C. The resulting tert-butanol is distilled off at 0° C. under reduced pressure. A solution of 7.02 g of 3-formyl-2-methylbenzyl tetrahydro-2-pyranyl ether in 10 ml of heptane is added dropwise at 5°-10° C. in the course of 30 minutes, and stirring is carried out for 2 hours at 5° C. and for 15 hours at room temperature. The precipitated solid is filtered off and the solution is evaporated down. After purification by column chromatography over silica gel using toluene as the mobile phase, 2.3 g of the desired ether are obtained.

Method B:

33.1 ml (0.053 mol) of n-butyllithium (15% strength solution in hexane) and then 11.7 g of 3-formyl-2-methylbenzyl tetrahydro-2-pyranyl ether in 10 ml of 1:1 ether/tetrahydro-furan are added dropwise at −100° C. to a solution of 12.8 g of diethyl trichloromethylphosphonate in 45 ml of ether and 35 ml of tetrahydrofuran under a nitrogen atmosphere. The stirred mixture is allowed to warm up to room temperature and is refluxed for 1 hour. The reaction mixture is cooled to −50° C., 50 ml of 2N sulfuric acid are added and the mixture is poured into 300 ml of water and extracted several times with ether. The combined ether phases are washed with water, dried and evaporated down. After purification by column chromatography over silica gel using toluene as the mobile phase, 4.7 g of the desired compound are obtained.

NMR spectrum [300 MHz; CDCl$_3$; δ(ppm)]: 1.47–1.93 (6H); 2.25 (3H); 3.57 (1H); 3.92 (1H); 4.48 (1H); 4.72 (1H); 4.81 (1H); 6.95 (1H); 7.2 (1H); 7.35 (2H).

1. Synthesis of the 3-isoxazolylbenzyl derivatives IIIa 1.1 3-(Isoxazol-3′-yl)-2-methylbenzyl alcohol

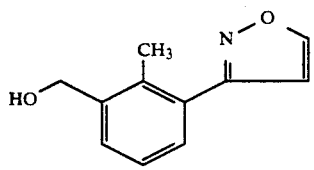

A 3-Hydroximinomethyl-2-methylbenzyl tetrahydro-2-pyranyl ether

A solution of 2.67 g of hydroxyladine hydrochloride and 10 ml of water was added to a solution of 6.0 g of 3-formyl-2-methylbenzyl tetrahydro-2-pyranyl ether and 50 ml of toluene at 25° C. After the addition of 2.01 g of sodium carbonate in 10 ml of H$_2$O, stirring was carried out overnight at 25° C. The product which had crystallized out in the course of the reaction was filtered off and dissolved in ether. 6.4 g of product were obtained from the combined organic phases after washing and drying. NMR spectrum [300 MHz; CDCl$_3$; δ(ppm)]: 1.2–1.85 (6H); 2.32 (3H); 3.50 (1H); 3.78 (1H); 4.40–4.85 (3H); 7.05–7.7 (3H); 8.42 (1H); 11.27 (1H).

B 3-(Isoxazol-3′-yl)-2-methylbenzyl tetrahydro-2-pyranyl ether

Acetylene was passed into a solution of 6.23 g of 3-hydroximinomethyl-2-methylbenzyl tetrahydro-2-pyranyl ether and 50 ml of CH$_2$Cl$_2$ at from 0° to 5° C. in the course of 30 minutes. Thereafter, 20.6 ml of a 10% strength sodium hypochlorite solution, to which a pinch of sodium acetate has been added, were introduced dropwise at 10° C. with continued passage of acetylene. After the end of the addition, acetylene was passed in for a further 15 minutes at 10° C. Stirring was then carried out for 1 hour at 10° C. After 14 hours at 25° C., the two phases were separated off. 4.8 g of product were obtained from the organic phase by washing, drying and purification by column chromatography (silica gel; 97.5:2.5 toluene/acetone).

NMR spectrum [250 MHz; CDCl$_3$; δ(ppm)]: 1.40–2.0 (6H); 38 (3H); 3.55 (1H); 3.92 (1H); 4.45–4.90 (3(1H); 6.48 (1H); 7.20–7.50 (3H); 8.43 (1H).

C 4.7 g of 3-(isoxazol-3′-yl)-2-methylbenzyl tetra hydro-2-pyranyl ether dissolved in 40 ml of methanol were stirred with 2.72 ml of concentrated hydrochloric acid for 14 hours at 25° C. Neutralization was then effected with sodium methylate solution while cooling with ice, and the neutral solution was evaporated down under reduced pressure. Water was added to the residue and the solution was extracted several time with diethyl ether. 3.0 g of 3-(isoxazol-3′-yl)-2-methylbenzyl alcohol were obtained from the combined ether extracts NMR spectrum [300 MHz; CDCl$_3$; δ(ppm)]: 2.25 (3H); 2.70 (1H) 4.65 (2H); 6.43 (1H); 7.15–7.50 (3H); 8.27 (1H).

2. Synthesis of the 3-isoxazolylbenzyl derivatives IIIb 2.1. 3-(3′-Ethylisoxazol-5′-2-methylbenzyl alcohol

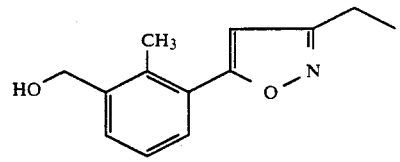

A 3-Ethynyl-2-methylbenzyl tetrahydro-2-pyranyl ether 19.7 ml of a 1.6 molar solution of n-butyllithium in n-hexane were added at −78° C. to a solution of 5.85 g of 3-(2′,2′-dibromovinyl)-2-methylbenzyl tetrahydro-2-pyranyl ether and 50 ml of tetrahydrofuran. After 1 hour at −78° C., the mixture was left for 1 hours at 25° C. and the reaction solution was then added to 300 ml of ice water. The mixture thus obtianed was extraced with diethyl ether. 3.1 g of the product (80% purity according to NMR) were obtained from the combined organic phases after washing, drying and chromatographic purification (silica gel/toluene).

NMR spectrum [200 MHz; CDCl$_3$; δ(ppm)]: 1.40–2.00 (6H); 2.48 (3H); 3.30 (1H); 3.60 (1H); 3.95 (1H); 4.40–4.95 (3H); 7.1–7.55 (3H).

3-(3′-Ethylisoxazol-5′-yl)-2-methylbenzyl tetrahydro-2-pyranyl ether

A solution of 3.43 g of nitropropane and 10 ml of toluene were added to a mixture of 9.2 g of phenyl isocyanate, 10.6 g of 3-ethynyl-2-methylbenzyl tetrahydro-2-pyranyl ether and 20 ml of toluene at 25° C., and 3 drops of triethylamine were added. After 14 hours at 25° C., the mixture was heated for 2 hours at 100° C. After cooling to 25° C., the reaction mixture was freed from solid constituents. 2.3 g of the product were obtained from the resulting solution after chromatography [silica gel; 98:2 toluene/acetone].

NMR spectrum [300 MHz; CDCl$_3$; δ(ppm)]: 1.36 (3H); 1.42–1.95 (6H); 2.21 (3H); 2.75 (2H); 3.55 (1H); 3.92 (1H); 4.4–4.9 (3H); 6.23 (1H); 7.0–7.6 (3H).

C 2.3 g of 3-(3′-ethylisoxazol-5′-yl)-2-methylbenzyl tetrahydro-2-pyranyl ether, dissolved in 40 ml of methanol, were stirred with 1.22 ml of concentrated hydrochloric acid for 14 hours at 25° C. Thereafter, the mixture was neutralized with sodium methylate solution while cooling with ice and the neutral solution was evaporated down under reduced pressure. Water was added to the residue and the solution was extracted several times with diethyl ether. 1.4 g of 3-(3′-ethylisoxazol-5′-yl)-2-methylbenzyl alcohol were obtained from the combined ether extracts.

NMR spectrum [300 MHz; CDCl$_3$; δ(ppm)]: 1.33 (2H); 2.37 (3H); 3.75 (2H); 4.72 (2H); 6.21 (1H); 7.2–7.6 (3H).

3. Synthesis of the 3-isoxazolylbenzyl esters Ia and Ib 3.1 3-(Isoxazol-3'-yl)-2-methylbenzyl cis,trans-3-(2'chloro-3',3',3'-trifluoroprop-1'-enyl)-2,2-dimethylcyclopropane-1-carboxylates

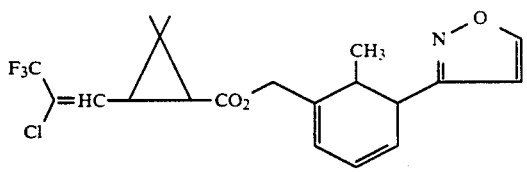

4.4 g of 3-(2'-chloro-3',3',3'-trifluoroprop-1'-enyl)2,2-dimethylcyclopropane-1-carbonyl chloride (cis-/trans=1:1) were added dropwise to a mixture of 3.0 g of 3-(isoxazol-3'-yl)-2-methylbenzyl alcohol, 1.67 g of picoline and 30 ml of tetrahydrofuran at 20° C. After the exothermic reaction had died down and stirring had been carried out for a further 5 hours, the reaction mixture was freed from solid residues. 5.1 g of product were obtained from the solution.

NMR spectrum [200 MHz; $CDCl_3$; $\delta$(ppm)]: 1.20-1.40 (6H); 1.83; 2.02; 2.18. 2.37 ($\Sigma$3H); 2.40 (3H); 5.10 (2H); 6.08; 6.95 ($\Sigma$1H); 6.60 (1H); 7.20-7.5 (3H); 8.50 (1H). Active ingredient Example 1.005

TABLE 1

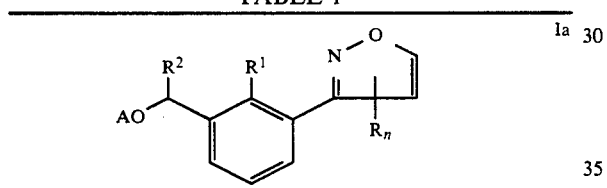

Ia

| Example No. | A | $R^1$ | $R^2$ | $R_n$ | Phys. date [mp. (°C.); NMR ($\delta$ in ppm)] | Isomer (A-OH) |
|---|---|---|---|---|---|---|
| 1.001 | A.002 | $CH_3$ | H | — | (300MHz; $CDCl_3$) 1.08-1.40(6H); 1.67-2.33(2H); 2.38(3H); 5.20(2H); 5.63(0.5H); 6.28 (0.5H); 6.49(1H); 7.25-7.58(3H); 8.47 (1H) | mixture |
| 1.002 | A.004 | $CH_3$ | H | — | (300MHz; $CDCl_3$) 1.07-1.42(6H); 1.65-2.37(2H); 2.40(3H); 5.20(2H); 6.17(0.9H); 6.48 (1H); 6.80(0.1H); 7.1-7.6(3H); 8.45 (1H) | mixture |
| 1.003 | A.005 | $CH_3$ | H | — | (200MHz; $CDCl_3$) 1.1-1.3(6H); 1.42-2.15(2H); 2.38 (3H); 3.95-4.80(1H); 5.18(2H); 6.50(1H); 7.20-7.57(3H); 8.50 (1H) | mixture |
| 1.004 | B.001 | $CH_3$ | H | — | (300MHz; $CDCl_3$) 0.70(3H); 1.02(3H); 2.10-2.50(1H); 2.25 (3H); 3.18(1H); 5.17 (2H); 6.43(1H); 7.10-7.55(7H); 8.47 (1H) | mixture |
| 1.005 | A.003 | $CH_3$ | H | — | (200MHz; $CDCl_3$) 1.20-1.40(6H); 1.83; 2.02; 2.18; 2.37(2H) 2.40(3H); 5.10(2H); 6.08; 6.95(1H); 6.60 | mixture |

TABLE 1-continued

Ia

| Example No. | A | $R^1$ | $R^2$ | $R_n$ | Phys. date [mp. (°C.); NMR ($\delta$ in ppm)] | Isomer (A-OH) |
|---|---|---|---|---|---|---|
| 1.006 | A.003 | $CH_3$ | H | — | (1H); 7.20-7.5(3H); 8.50(1H) (200MHz; $CDCl_3$) 1.30(6H); 1.95-2.30 (2H); 2.40(3H); 5.17(2H); 6.5(1H); 6.93(1H); 7.20-7.50 (3H); 8.50(1H); | cis* |
| 1.007 | A.003 | $CH_3$ | H | — | (300MHz; $CDCl_3$) 1.15-1.40(6H); 1.75-1.85(2H); 2.40 (3H); 5.22(2H); 5.90-6.15(1H); 6.50(1H); 7.20-7.60(3H); 8.50(1H) | trans* |

*with regard to stereochemistry at the cyclopropane ring

TABLE 2

Ib

| Example No. | A | $R^1$ | $R^2$ | $R_n$ | Phys. data [mp. (°C.); NMR [$\delta$ in ppm)] | Isomer (A-OH) |
|---|---|---|---|---|---|---|
| 2.001 | A.002 | $CH_3$ | H | 3-$CH_2CH_3$ | (300MHz; $CDCl_3$) 1.10-1.50 (9H); 1.80-2.40 (2H); 2.38 (3H); 3.78(2H); 5.21(2H); 6.18(0.5H); 6.24(1H); 6.90(0.5H); 7.20-7.60 (3H); | mixture |

USE EXAMPLES

The insecticidal action of the 3-isoxazolyl benzyl esters of the general formulae Ia and Ib were demonstrated by the following experiments:

The active ingredients were prepared
a) as a 0.1% strength solution in acetone or
b) as a 10% strength emulsion in a mixture of 70% by weight of cyclohexanol, 20% by weight of Nekanil ® LN (Lutensol ® AP6, wetting agent having an emulsifying and dispersant effect and based on ethoxylated alkylphenols) and 10% by weight of Emulphor ® EL (Emulan ® EL, emulsifier based on ethoxylated fatty alcohols) and were diluted with acetone in the case of a) and with water in the case of b), depending on the required concentration.

EXAMPLE A

*Blatta orientalis* (oriental cockroach)

Contact action

The bottom of 1 l glass vessel (diameter about 10 cm) was covered with a solution of the active ingredient in acetone. After the solvent had evaporated off, 5 adult cockroaches were placed in the glass vessel. After 48 hours, the kill rate in % was determined.

In this experiment, compounds No. 1.001, No. 1.002, No. 1.003, No. 1.005 and No. 2.001 had kill rates of from 80 to 100% at an active ingredient concentration of from 0.04 to 1 mg.

EXAMPLE B

*Plutella maculipennis* (caterpillar of diamondback moth)

Contact action

Leaves of young cabbage plants were dipped briefly (for 3 sec) into the aqueous active ingredient emulsion, allowed to drip off and then placed on a moistened filter in a Petri dish. 10 caterpillars in the 4th stage of development were placed on the leaves prepared in this manner in each Petri dish. After 48 hours, the kill rate in % was determined.

In this experiment, compounds No. 1.001, No. 1002, No. 1.003, No. 1.004 and No. 2.001 had kill rates of from 60 to 100% at an active ingredient concentration of from 20 to 1,000 ppm.

EXAMPLE C

*Tetranychus telarius* (red spider)

Contact action

Highly infested potted bush beans which had the second pair of secondary leaves were sprayed to run-off with the aqueous active ingredient formulation. After 5 days in the greenhouse, the success of control in % was determined by means of a binocular microscope.

In this experiment, compounds No. 1.001, No. 1002, No. 1.003, No. 1.004, No. 1.005 and No. 2.001 showed from 80 to 100% of success in control at an active ingredient concentration of from 4 to 1000 ppm.

We claim:

1. A 3-isoxazolylbenzyl ester of the formula Ia or Ib

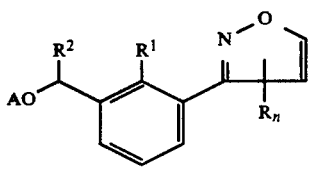

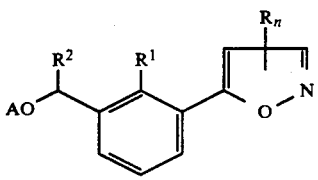

where

R is halogen, $C_1$–$C_4$-alkyl, $C_1$–$C_4$-haloalkyl, $C_1$–$C_4$-alkoxy, $C_1$–$C_4$-haloalkoxy, $C_2$–$C_4$-alkenyl or $C_2$–$C_4$-haloalkenyl or is phenylethyenyl which may carry from one to five halogen atoms, or is $C_2$–$C_4$-alkynyl, $C_3$–$C_6$-cycloalkyl, phenyl, naphthyl, phyrrolyl, pyrazolyl, imidazolyl, isoxazolyl, oxazolyl, isothiazolyl, thiazolyl, furanyl, thienyl or pyridyl, $CO_2R^3$ or $CONR^4R^5$, $R^3$, $R^4$ and $R^5$ are each hydrogen or $C_1$–$C_6$-alkyl, n is 0, 1 or 2, and the radicals R may be different when n is 2, $R^1$ is halogen or $C_1$–$C_4$-alkyl, $R^2$ is hydrogen, $C_1$–$C_4$-alkyl, $C_2$–$C_4$-alkenyl, $C_2$–$C_4$-alkynyl or cyano and A is a carbonyl radical of the formula IIa or IIb

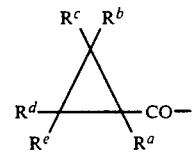

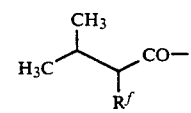

where $R^a$ is hydrogen, $C_1$–$C_4$-alkyl or phenyl, wherein the aromatic ring may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, $R^b$–, $R^c$ and $R^d$ are each hydrogen, halogen or $C_1$–$C_4$-alkyl, $R^e$ is hydrogen, halogen, $C_1$–$C_4$-alkyl or $C_1$–$C_4$-haloalkyl or is $C_2$–$C_6$-alkenyl or $C_2$–$C_6$-alkadienyl which may carry from one to eight halogen atoms and/or one of the following radicals: $C_1$–$C_4$-alkoxycarbonyl or phenyl, where the phenyl radical in turn may carry from one to five halogen atoms and/or from one to three of the following groups: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $R^e$ is $C_3$–$C_7$-cycloalkylidenemethyl, or $R^d$ and $R^e$ together form a 2,2,H-indenespiro group $R^f$ is phenyl, 1-pyrrolyl or 2-isoindolyl radical, where this ring system may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or a phenylamino group where the phenyl ring in turn may carry from one to five halogen atoms and/or from one to three of the following radicals:

$C_1$–$C_4$-alkyl, $C_1$–$C_4$-haloalkyl, $C_1$–$C_4$-alkoxy, $C_1$–$C_4$-haloalkoxy or $C_1$–$C_4$-alkythio.

2. A 3-isoxazolylbenzyl ester of the formula Ia or Ib as defined in claim 1 wherein $R^1$ is methyl or ethyl and $R^2$ is hydrogen.

3. A 3-isoxazolylbenzyl ester of the formula Ia or Ib as defined in claim 1, where $R^1$ is methyl or ethyl, $R^2$ is hydrogen and n is 0.

4. A 3-isoxazolylbenzyl ester of the formula Ia or Ib as defined in claim 1, wherein A is the carbonyl radical of a pyrethroid acid of the formula IIa where $R^a$ and $R^d$ are each hydrogen, $R^b$ and $R^c$ are each methyl and $R^e$ is $C_2$–$C_4$-alkenyl which may carry from two to six halogen atoms.

5. A 3-isoxazolylmethyl derivative of the formula IIIa or IIIb

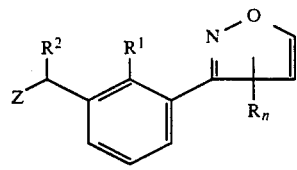

IIIa

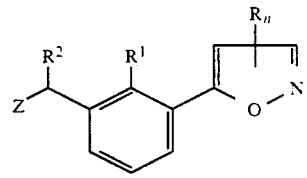

where R, R$^1$ and R$_2$ and n have the meanings stated in claim 1 and Z is hydroxyl or halogen.

6. A pesticidal composition containing an effective amount of a 3-isoxazolylbenzyl ester of the formula Ia or Ib as defined in claim 1 and inert additives.

7. A method for controlling pests, wherein the pests and/or their habitat are or is treated with an effective amount of a 3-isoxazolylbenzyl ester of the formula Ia or Ib as defined in claim 1.

* * * * *